United States Patent
Chen et al.

(10) Patent No.: US 10,363,075 B2
(45) Date of Patent: Jul. 30, 2019

(54) POROUS BIONIC INTERNAL FIXATION DEVICE FOR PROMOTING HEALING OF FRACTURED BONE

(71) Applicants: Yingze Zhang, Shijiazhuang, Hebei Province (CN); Wei Chen, Shijiazhuang, Hebei Province (CN)

(72) Inventors: Wei Chen, Shijiazhuang (CN); Hongzhi Lv, Shijiazhuang (CN); Chenguang Du, Shijiazhuang (CN); Peizhi Yuwen, Shijiazhuang (CN); Yiyang Yu, Shijiazhuang (CN); Yingze Zhang, Shijiazhuang (CN)

(73) Assignee: Yingze Zhang, Shijiazhuang, Hebei (CN)

( * ) Notice: Subject to any disclaimer, the term of this patent is extended or adjusted under 35 U.S.C. 154(b) by 0 days.

(21) Appl. No.: 15/106,563

(22) PCT Filed: May 22, 2015

(86) PCT No.: PCT/CN2015/079605
§ 371 (c)(1),
(2) Date: Jun. 20, 2016

(87) PCT Pub. No.: WO2016/127522
PCT Pub. Date: Aug. 18, 2016

(65) Prior Publication Data
US 2016/0361102 A1    Dec. 15, 2016

(30) Foreign Application Priority Data

Feb. 9, 2015  (CN) .......................... 2015 1 0065992
Mar. 24, 2015  (CN) ..................... 2015 2 0166778 U

(51) Int. Cl.
*A61B 17/74*  (2006.01)
*A61B 17/86*  (2006.01)
(Continued)

(52) U.S. Cl.
CPC .......... *A61B 17/866* (2013.01); *A61B 17/683* (2013.01); *A61B 17/744* (2013.01);
(Continued)

(58) Field of Classification Search
CPC ............ A61B 17/72–748; A61B 17/8625–864
See application file for complete search history.

(56) References Cited

U.S. PATENT DOCUMENTS 4,259,072 A * 3/1981 Hirabayashi ......... A61C 8/0012
                                                  433/173
4,653,489 A * 3/1987 Tronzo ................. A61B 17/746
                                                  606/304
(Continued)

FOREIGN PATENT DOCUMENTS

CN         1266670 A       9/2000
CN       101342100 A       1/2009
(Continued)

OTHER PUBLICATIONS

International Search Report for International Application No. PCT/CN2015/079605, dated Oct. 23, 2015.
The Chineses 1OA issued by SIPO dated May 27, 2015.

*Primary Examiner* — Eduardo C Robert
*Assistant Examiner* — Michelle C Eckman
(74) *Attorney, Agent, or Firm* — Yunling Ren

(57) ABSTRACT

A porous bionic internal fixation device for promoting healing of a fractured bone includes a lag screw in a round rod shape, the lag screw is provided with fixation structures at both ends thereof, and on a body of the lag screw, a plurality of apertures directing laterally or obliquely are provided, and densely distributed micro-holes are provided on the body of the lag screw between the adjacent apertures. When in use, the both ends of the lag screw are respectively located in the bone at opposite sides of the fractured bone, so that the longitudinal direction of the apertures is aligned (Continued)

with the direction of the tensile trabeculae or the compressive trabeculae at the fractured bone, and the position of the apertures corresponds to the fractured bone.

20 Claims, 6 Drawing Sheets

(51) Int. Cl.
*A61B 17/68* (2006.01)
*A61B 17/80* (2006.01)
*A61B 17/84* (2006.01)
*A61B 17/00* (2006.01)

(52) U.S. Cl.
CPC ........ *A61B 17/746* (2013.01); *A61B 17/8033* (2013.01); *A61B 17/8061* (2013.01); *A61B 17/846* (2013.01); *A61B 17/86* (2013.01); *A61B 17/8625* (2013.01); *A61B 2017/00893* (2013.01)

(56) References Cited

U.S. PATENT DOCUMENTS

| | | | |
|---|---|---|---|
| 5,702,482 A | 12/1997 | Thongpreda et al. | |
| 6,312,467 B1* | 11/2001 | McGee | A61F 2/28 623/16.11 |
| 6,332,779 B1* | 12/2001 | Boyce | A61F 2/28 433/215 |
| 6,383,519 B1* | 5/2002 | Sapieszko | C04B 38/0025 424/401 |
| 7,354,442 B2* | 4/2008 | Sasso | A61B 17/8615 606/280 |
| 7,717,947 B1* | 5/2010 | Wilberg | A61B 17/864 606/304 |
| 8,137,350 B2* | 3/2012 | Nakamura | A61B 17/746 606/65 |
| 8,157,803 B1* | 4/2012 | Zirkle, Jr. | A61B 17/746 606/64 |
| 8,372,126 B2* | 2/2013 | Trieu | A61B 17/7098 606/304 |
| 8,435,240 B2* | 5/2013 | Yu | A61B 17/74 606/65 |
| 8,562,348 B2* | 10/2013 | Collins | A61C 8/0012 433/174 |
| 8,690,930 B2* | 4/2014 | Biedermann | A61B 17/7037 606/304 |
| 8,821,506 B2* | 9/2014 | Mitchell | A61M 31/00 606/271 |
| 9,095,396 B2* | 8/2015 | Collins | A61C 8/0012 |
| 9,101,321 B1* | 8/2015 | Kieser | A61B 17/7004 |
| 9,155,580 B2* | 10/2015 | Cormier | A61B 17/7037 |
| 9,173,692 B1* | 11/2015 | Kaloostian | A61B 17/8685 |
| 9,265,548 B2* | 2/2016 | Jones | A61B 17/7098 |
| 9,603,644 B2* | 3/2017 | Sweeney | A61B 17/864 |
| 9,668,798 B2* | 6/2017 | Giersch | A61B 17/8886 |
| 9,707,058 B2* | 7/2017 | Bassett | A61C 8/0012 |
| 9,744,007 B2* | 8/2017 | Lomicka | A61C 8/0033 |
| 9,775,702 B2* | 10/2017 | Arai | A61F 2/0811 |
| 2002/0045900 A1* | 4/2002 | Harder | A61B 17/744 606/65 |
| 2004/0010313 A1* | 1/2004 | Aston | A61F 2/28 623/17.11 |
| 2004/0122431 A1* | 6/2004 | Biedermann | A61B 17/864 606/62 |
| 2004/0267263 A1 | 12/2004 | May | |
| 2004/0267265 A1 | 12/2004 | Kyle | |
| 2005/0010226 A1* | 1/2005 | Grady, Jr. | A61B 17/746 606/281 |
| 2005/0015060 A1* | 1/2005 | Sweeney | A61B 17/864 604/264 |
| 2005/0015061 A1* | 1/2005 | Sweeney | A61B 17/7061 604/264 |
| 2005/0015154 A1* | 1/2005 | Lindsey | A61B 17/68 623/23.46 |
| 2006/0106386 A1* | 5/2006 | Reber | A61B 17/1721 606/65 |
| 2006/0121084 A1* | 6/2006 | Borden | A61B 17/866 424/426 |
| 2008/0269893 A1* | 10/2008 | Bhatnagar | A61B 17/7208 623/11.11 |
| 2009/0048675 A1* | 2/2009 | Bhatnagar | A61B 17/0642 623/17.16 |
| 2009/0082810 A1* | 3/2009 | Bhatnagar | A61B 17/7002 606/250 |
| 2009/0306666 A1* | 12/2009 | Czartoski | A61B 17/72 606/64 |
| 2010/0262089 A1* | 10/2010 | Sweeney | A61B 17/3472 604/272 |
| 2010/0266979 A1* | 10/2010 | Karmon | A61B 17/025 433/80 |
| 2011/0015684 A1* | 1/2011 | Belcheva | A61B 17/864 606/314 |
| 2011/0060373 A1* | 3/2011 | Russell | A61B 17/0401 606/304 |
| 2011/0093020 A1* | 4/2011 | Wu | A61B 17/866 606/304 |
| 2011/0208189 A1* | 8/2011 | Faccioli | A61B 17/72 606/62 |
| 2011/0313356 A1* | 12/2011 | Rabiner | A61B 17/7275 604/103.02 |
| 2012/0022603 A1* | 1/2012 | Kirschman | A61B 17/7064 606/305 |
| 2012/0041395 A1* | 2/2012 | Sweeney | A61B 17/7061 604/272 |
| 2012/0156477 A1* | 6/2012 | Kurze | A61L 27/047 428/336 |
| 2012/0197311 A1* | 8/2012 | Kirschman | A61B 17/7064 606/304 |
| 2012/0271362 A1* | 10/2012 | Martineau | A61B 17/863 606/304 |
| 2013/0245763 A1* | 9/2013 | Mauldin | A61F 2/4455 623/17.11 |
| 2013/0253661 A1* | 9/2013 | D'Agostino | A61K 9/0024 623/23.51 |
| 2014/0039565 A1* | 2/2014 | Martineau | A61B 17/8625 606/304 |
| 2014/0330274 A1* | 11/2014 | Matityahu | A61B 17/744 606/64 |
| 2014/0371748 A1* | 12/2014 | Yamanaka | A61B 17/742 606/64 |
| 2015/0127057 A1* | 5/2015 | Ganey | A61F 2/28 606/309 |
| 2015/0272646 A1* | 10/2015 | Russell | A61B 17/7098 606/304 |
| 2016/0022340 A1* | 1/2016 | Wayne | A61B 17/1725 606/304 |
| 2016/0106838 A1* | 4/2016 | D'Agostino | A61B 17/7233 623/23.51 |
| 2016/0193824 A1* | 7/2016 | James | B41F 1/18 101/453 |
| 2016/0346435 A1* | 12/2016 | D'Agostino | A61L 27/58 |
| 2016/0361102 A1* | 12/2016 | Chen | A61B 17/683 |
| 2017/0239396 A1* | 8/2017 | D'Agostino | A61L 27/58 |

FOREIGN PATENT DOCUMENTS

| | | | | |
|---|---|---|---|---|
| CN | 101569555 A | 11/2009 | | |
| CN | 101631515 A | 1/2010 | | |
| CN | 101716101 A | * 6/2010 | ............ | A61F 2/36 |
| CN | 201529176 U | 7/2010 | | |
| CN | 101843533 A | 9/2010 | | |
| CN | 201631366 U | 11/2010 | | |
| CN | 104302237 A | 1/2015 | | |
| CN | 104586496 A | 5/2015 | | |

\* cited by examiner

POROUS BIONIC INTERNAL FIXATION DEVICE FOR PROMOTING HEALING OF FRACTURED BONE

CROSS REFERENCE

The present application is a continuing application of International Application No. PCT/CN2015/079605, filed on May 22, 2015, which is based upon and claims priority to Chinese Patent Application No. 201510065992.0, filed on Feb. 9, 2015 and Chinese Patent Application No. 201520166778.X, filed on Mar. 24, 2015, and the entire contents thereof are incorporated herein by reference.

TECHNICAL FIELD

The present invention relates to a fixation device for treating a fractured bone, and belongs to the technical field of orthopedics medical instruments.

BACKGROUND

In the treatment of fracture, how to carry out reduction and fixation according to bone structures is a very important factor, which will directly influence on the process and quality of fracture union, and is critical to the success of the operation. In view of anatomy, a bone mainly composes of a periosteum, a cortical bone, a cancellous bone, and so on. The cortical bone is compact and solid, has strong compression resistance, and located at outside. The cancellous bone is located inside the bone, is consisted of structure tissues, such as bone trabeculae, interwoven into a network, and has a loose structure. The bone trabeculae are mostly arranged in a direction consistent with a direction of stress which the bone is withstood. At different parts, the bone trabeculue are extended in different directions. The bone trabeculae in the proximal femur may be classified into primary tensile trabeculae, secondary tensile trabeculae, primary compressive trabeculae and secondary compressive trabeculae. For bones of a human body, according to the rule during the union and remodeling of the fractured bone, if displacement occurred after fracture, callus will be significantly formed at the compression side, and the bone trabeculae therein will be arranged in a direction in which compression stress is transferred, while at the tension side, absorption of bone will occurred and the structure of the bone trabeculae becomes loose.

After a conventional fracture internal fixation device is implanted, the bone trabeculae at broken ends will be destroyed due to the occupying effect of the implanted device, the growth and recovery to its continuity of the bone trabeculae at the broken ends will be influenced, and callus inside and outside of a bone marrow will not grow in balance way, especially for the aged people who suffers from osteoporotic fracture, it is possible that after the cortex of the bone is healed, the cancellous bone is still poorly healed, and the cancellous bone in the medullary cavity may not be fully recovered to its continuity, it will influence transmission of normal load and is likely to cause stress concentration, will also influence the overall strength of the healed bone, and sometimes, it is possible to result in delayed union or nonunion.

With the continuously development of the internal fixation technology of the orthopedics, it is really necessary to design a new fixation device enabling the cortex of the fractured bone and the primary bone trabeculae to be remolded at the same time so that the fracture may be healed both inside and outside of the marrow at the same time, by guiding the treatment of the fracture under the principle of the biology and the biomechanics. Whereby, the healing rate of the fracture may be speeded up, the healing quality and strength of the fracture may be improved, and the rate of occurrence of complications, such as fracture nonunion, delay union, loose or rupture of the internal fixation device, and so on may be lowered down.

The foresaid information as disclosed in the background part only serves to enhance understanding of the background of the disclosure, thereby it may not contain ordinary skill information that has been well known.

SUMMARY

A technical problem to be solved by the present disclosure is to provide a porous bionic internal fixation device for promoting healing of a fractured bone, the porous bionic internal fixation device enables the cortex and the bone trabeculae of the fractured bone to be grown and remolded at the same time by taking advantage of the bionic internal fixation theory, allows the fractured bone being healed both inside and outside of the marrow at the same time, and achieves a satisfactory reduction, fixation and healing result of the fracture.

Additional aspects and advantages of the disclosure will be in part set forth in the description below, and in part will become obvious from the description, or may be learned from practice of the present disclosure.

In order to achieve the above mentioned objectives, in the present disclosure, the following technical solution is employed:

According to an aspect of the present disclosure, a porous bionic internal fixation device for promoting healing of fracture is provided, it includes a lag screw in a round rod shape, the lag screw is provided with fixation structures at both ends thereof, and on a body of the lag screw, a plurality of apertures directing laterally or obliquely are provided, and densely distributed micro-holes are provided on the body of the lag screw between the adjacent apertures. When in use, the both ends of the lag screw are respectively located in the bone at opposite sides of the fractured bone, so that the longitudinal direction of the apertures is aligned with the direction of the tensile trabeculae or the compressive trabeculae at the fractured bone, and the position of the apertures corresponds to the fractured bone.

According to an embodiment of the present disclosure, the plurality of apertures are arranged in parallel along the longitudinal direction, or transverse direction, or oblique direction of the lag screw.

According to an embodiment of the present disclosure, each of the apertures has a diameter of about 0.1 to about 3 mm, and each of the micro-holes has a diameter of about 1 to about 50 um.

According to an embodiment of the present disclosure, when in use, the apertures at the fractured partial part are arranged in directions respectively consistent with the directions of the primary tensile trabeculae, the secondary tensile trabeculae, the primary compressive trabeculae and the secondary compressive trabeculae.

According to an embodiment of the present disclosure, the apertures and/or the micro-holes are filled with magnesium alloy for promoting healing of the fractured bone.

According to an embodiment of the present disclosure, the lag screw is provided with a through hole therein along its longitudinal direction.

According to an embodiment of the present disclosure, the internal fixation device further comprises a femur fixation main nail, the femur fixation main nail is provided with a connection through hole, the lag screw is inserted in the connection through hole of the femur fixation main nail, and an angle formed between the femur fixation main nail and the lag screw is about 90°-about 140°, the femur fixation main nail is provided with a through hole therein along its transverse direction.

According to an embodiment of the present disclosure, a plurality of apertures provided laterally or obliquely are provided on the femur fixation main nail, so that longitudinal directions of the apertures are consistent with directions of the tensile trabeculae or the compressive trabeculae at the fractured bone and the position of the apertures corresponds to the fractured bone, and densely distributed micro-holes are provided on a body of the femur fixation main nail, between the adjacent apertures.

According to an embodiment of the present disclosure, the femur fixation main nail is provided with a notch at one end thereof, and the notch is perpendicular to a central line of the femur fixation main nail.

According to an embodiment of the present disclosure, the apertures and/or the micro-holes are filled with magnesium alloy for promoting healing of the fractured bone.

According to an embodiment of the present disclosure, the plurality of apertures are arranged in parallel along the longitudinal direction of the femur fixation main nail.

According to an embodiment of the present disclosure, the apertures each has a diameter of about 0.1 to about 3 mm, and the micro-holes each has a diameter of about 1-about 50 um.

According to an embodiment of the present disclosure, the internal fixation device further comprises a connection steel plate on which a hole for passing the lag screw is provided.

According to an embodiment of the present disclosure, the fixation structure at one end of the lag screw is a fixation thread or a locking nut matched with a thread on the lag screw, and the fixation structure at the other end is a fixation thread or a nail head integrated with the lag screw.

From the above technical solution, it may be seen that the beneficial effect of the present disclosure is as follows:

According to the present disclosure, the tensile fixation nails connecting the opposite sides of the fractured bone are respectively provided with the apertures and the densely distributed micro-holes, the longitudinal direction of the apertures are consistent with the direction of the primary bone trabeculae at the local bone, and the densely distributed micro-holes are provided between the apertures, furthermore, the apertures and the micro-holes are filled with magnesium alloy for promoting healing of the fractured bone. This structure allows the bone trabeculae to grow along the apertures and the micro-holes in the lag screw, enables the callus to grow both inside and outside the marrow simultaneously, shortens healing period of the fractured bone, and reduces various complications accompanied with the fracture and operation. At the same time, the densely distributed micro-holes, combining with the plurality of apertures, allow the lag screw to have a greater elastic modulus, avoid the internal fixation strength to be impaired, and prevent the occurrence of the situations such as nail broken, stress fracture, and so on. The apertures and the micro-holes are filled with magnesium alloy subjected from micro-arc oxidation process, this kind of magnesium alloy may be absorbed gradually after the operation, whereby it facilitates the bone trabeculae to grow in the apertures and the micro-holes, effectively promotes healing of the fractured bone, and more complies with the biology force requirement for healing of the fractured bone.

In the present disclosure, the bionic internal fixation theory is employed, and the bionic internal fixation device more complying with the bone autonomy structure, in particularly complying with the biomechanics structure characteristics may be used, so that the fractured bone may be recovered following its own conduction and load characteristics, and the fracture treatment may achieve the satisfactory reduction and healing result.

With the creative invention of the fracture reduction and fixation technology according to the present disclosure, the problem that the cancellous bone is poorly healed after the treatment of the fracture, especially, the osteoporotic fracture of an aged people, the healing strength of the bone is influenced, and sometimes, possibly to cause the delay healing of the fractured bone or even re-fracture, is solved.

The porous bionic internal fixation device according to the present disclosure is suitable for internal fixation treatment for fractured bones all over the whole body, especially for complicated bone trabeculae structural fracture near joints, combining with the support from the mini-invasive technology and the image navigation technology, the porous bionic internal fixation device according to the present disclosure has good anticipation and may achieve significant economic and social benefit.

BRIEF DESCRIPTION OF THE DRAWINGS

The above and other objectives, features and advantages of the present disclosure will become more apparent by describing the preferred embodiments of the present disclosure below, with reference to the attached drawings.

Figure 1:
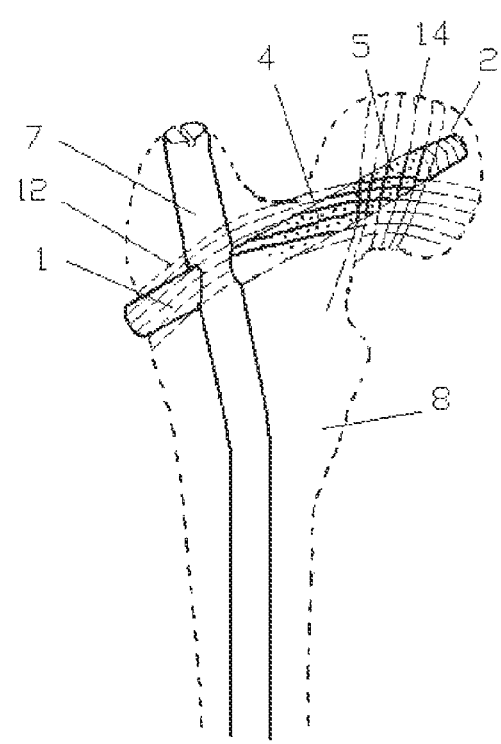
FIG. 1 is a schematic diagram showing a usage state in which the porous bionic internal fixation device for promoting healing of a fractured bone according to the present disclosure is applied to a proximal femoral fracture.

DESCRIPTION OF THE REFERENCE NUMERALS lag screw 1
internal fixation thread 2
locking nut 3
aperture 4
micro-hole 5 notch 6
femur fixation main nail 7
femur 8
tibia 9
calcaneus 10
steel plate 11
primary tensile trabeculae 12
secondary tensile trabeculae 13
primary compressive trabeculae 14
secondary compressive trabeculae 15.

DETAILED DESCRIPTION

Now, exemplary embodiments of the present disclosure will be more fully described with reference to the attached drawings. However, the exemplary embodiments may be implemented in various ways, and should not be construed as being limited to the embodiments set forth herein, rather, these embodiments are provided so that the present disclosure will be thorough and complete, and will fully convey the scope of the present disclosure to the person skilled in the related art. Throughout the drawings, the same reference numerals are used to refer to the same or similar structure, and thus its detail description will be omitted as necessary.

The porous bionic internal fixation device for promoting healing of a fractured bone according to the present disclosure includes a lag screw 1 in round rod shape, the lag screw 1 may be provided with a through hole at its center, the lag screw 1 is provided with an internal fixation thread 2 at one end and a locking structure at the other end, the both ends of the lag screw 1 are respectively located in the bone at opposite sides of a fracture part, and the lag screw 1 is also provided with apertures 4 and micro-holes 5 therein. The porous internal fixation device for promoting healing of a fractured bone according to the present disclosure may further include a femur fixation main nail 7 on which apertures 4 and micro holes 5 are provided. Hereinafter, the present disclosure will be described in detail in connection with its particular application.

As shown in FIG. 1, FIG. 1 is a schematic diagram showing a usage state in which the porous bionic internal fixation device for promoting healing of a fractured bone according to the present disclosure is applied to a proximal femoral fracture. When the internal fixation device of the present disclosure is applied in the proximal femoral fracture, it may include the lag screw 1 and the femur fixation main nail 7. The tensile fixation nail 1 is provided with apertures laterally or obliquely on its body, both ends of the apertures are opened at both sides of the body of the lag screw 1, the apertures 4 may or may not pass through the central axis of the lag screw 1, and longitudinal direction of the apertures may be consistent with direction of tensile bone trabeculae or compressive trabeculae, FIG. 1 shows the primary tensile bone trabeculae 12, the secondary tensile bone trabeculae 13, the primary compressive trabeculae 14 and the secondary compressive trabeculae 15. A plurality of apertures 4 are arranged along the longitudinal direction, or transverse direction, or oblique direction of the lag screw 1 in parallel, and the apertures are positioned corresponding to the fractured bone. The micro-holes 5 are distributed over the body of the lag screw 1 between the adjacent apertures 4, the apertures each has a diameter of 0.1 to 3 mm and the micro-holes 5 each has a diameter of 1 to 50 um. This structure may allow the bone trabeculae to grow along the apertures 4 and micro-holes 5 of the lag screw 1, enable callus to grow simultaneously both inside and outside of marrow, shorten the healing period of the fractured bone, and reduce various complications accompanied with the fracture and operation. At the same time, combining with the plurality of apertures 4, the structure of the micro-holes 5 enables the lag screw 1 to have a better elastic modulus, avoids weakening internal fixation strength, and prevents the situations such as nail broken, stress fracture, and so on.

In an embodiment, the apertures 4 and the micro-holes 5 are filled with magnesium alloy for promoting healing of the fractured bone. This kind of magnesium alloy has been subjected from micro-arc oxidation process, start to be absorbed in 4-6 months after operation, and will be fully absorbed over 1 to 3 months, so as to provide the bone trabeculae with space for growing, facilitate the bone trabeculae to grow in the apertures and micro-holes, more efficiently promote healing of the fracture, and more comply with the biomechanics requirement for healing of the fracture.

The femur fixation main nail 7 is provided with a connection through hole through which the lag screw 1 is inserted, and the femur fixation main nail 7 is provided with a through hole along its longitudinal direction or transverse direction. The femur fixation main nail 7 is provided with a notch 6 at its end surface located at outside of the femur, the notch 6 is perpendicular to the center of the end surface, and is extended in a direction consistent with the longitudinal direction of the apertures 4. The notch 6 is convenient to guide the operator to find a suitable direction of the bone trabeculae at the broken ends of the fractured bone, so as to adjust direction in which a needle is advanced.

As shown in FIG. 1, when a fractured femur neck is reducted and fixed, the tensile fixation nail 1 is a fixation nail connecting both sides of the fractured femur neck. An end of the lag screw 1 on which the internal fixation thread 2 is provided is connected with the fractured caput femoris, and the locking structure at the other end of the tensile fixation nail 1 is connected at outside of the femur 8, the apertures 4 of the tensile fixation nail 1 are positioned at both sides of the fractured femur neck, and the apertures are respectively oriented in the direction consistent with the primary tensile bone trabeculae 12 and the primary compressive trabeculae 14. In the femur 8, the femur fixation main nail 7 is provided along the longitudinal direction of the femur 8, the femur fixation main nail 7 is provided with a connection hole at its upper portion, the connection hole has a diameter matched with the outer diameter of the tensile fixation nail 1, so that the tensile fixation nail 1 may be inserted into the connection hole of the femur fixation main nail 7, and an angle between the longitudinal direction of the femur fixation main nail 7 and the longitudinal direction of the tensile fixation nail 1 is about 90 to about 140 degree.

Figure 2:
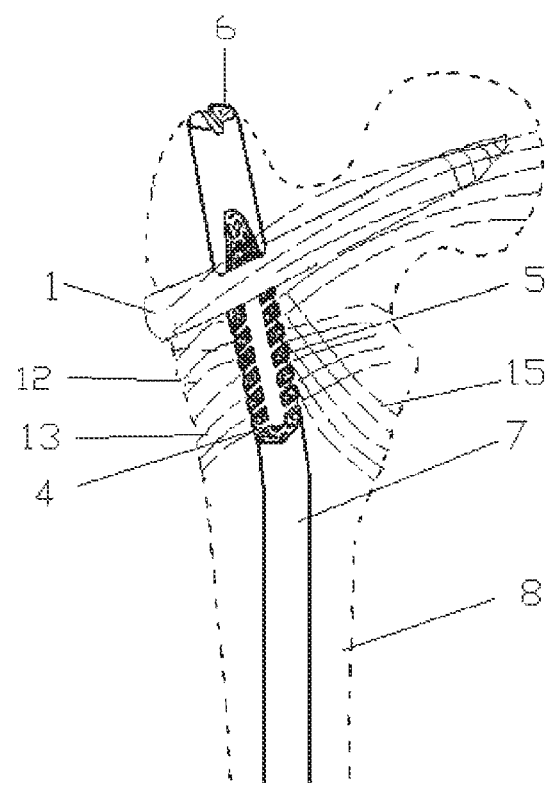
FIG. 2 is a schematic diagram showing a usage state in which the porous bionic internal fixation device for promoting healing of a fractured bone according to the present disclosure is applied to a proximal femoral fracture.

As shown in FIG. 2, FIG. 2 is a schematic diagram showing a usage state in which the porous bionic internal fixation device for promoting healing of a fractured bone according to the present disclosure is applied to another proximal femoral fracture. As shown in FIG. 2, when the proximal end of the femur 8 is reduted and fixed, the lag screw 1 is a fixation nail for connecting both sides of the fractured femur 8, the femur fixation main nail 7 is fixed along the longitudinal direction of the femur, an upper end of the femur fixation main nail 7 is connected at the top end of the femur 8, an lower end of the femur fixation main nail 7 is connected in a fractured portion of the femur 8, the tensile fixation nail 1 may not be provided with the apertures, but the femur fixation main nail 7 may be provided with the apertures thereon. The apertures 4 of the femur fixation main nail 7 are positioned at both sides of the fractured femur 8, and the direction of the apertures 4 is consistent with the direction of the primary tensile bone trabeculae 12 and the secondary tensile bone trabeculae 13 in the femur 8, and densely distributed micro-holes may be respectively provided on the body of the femur fixation main nail 7 between the adjacent apertures. An end surface of the tensile fixation nail 1 located outside of the femur 8 is provided with a notch 6, the notch 6 is perpendicular to the center of the end surface, and is extended in a direction consistent with the longitudinal direction of the apertures 4.

Figure 3:
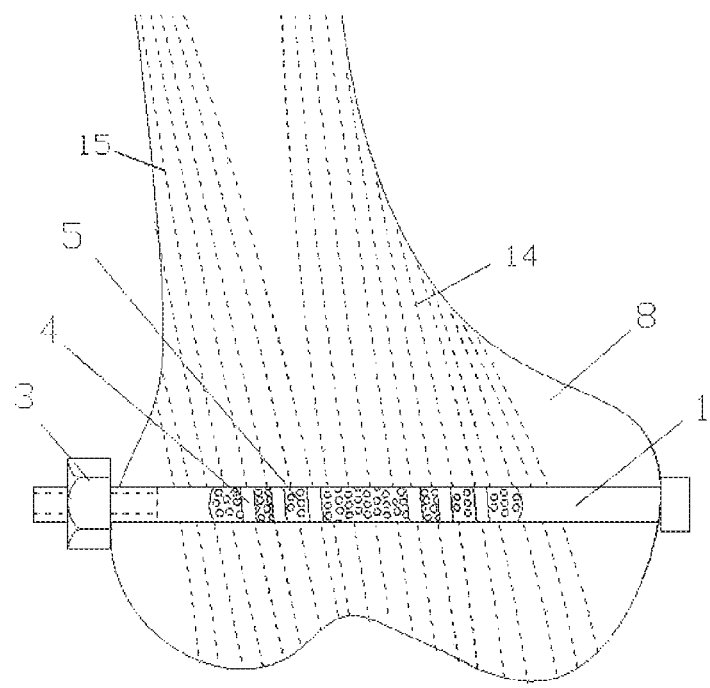
FIG. 3 is a schematic diagram showing a usage state in which the porous bionic internal fixation device for promoting healing of a fractured bone according to the present disclosure is applied to a distal femoral fracture.

As shown in FIG. 3, FIG. 3 is a schematic diagram showing a usage state in which the porous bionic internal fixation device for promoting healing of a fractured bone according to the present disclosure is applied to a distal femoral fracture. As shown in FIG. 3, when a distal end of the femur 8 is reduced and fixed, the tensile fixation nail 1 is a fixation nail for connecting both sides of the fractured femur 8, one end of the tensile fixation nail 1 is a nail head, and the locking structure on the other end is a locking nut 3, the tensile fixation nail 1 is perpendicular to the longitudinal direction of the femur 8, and the direction of the apertures 4 is consistent with the direction of the primary bone trabeculae in the femur 8.

In the tensile fixation nail 1 according to the present disclosure, the apertures 4 and the micro-holes 5 are arranged on the body of the tensile fixation nail 1 in a length range of about 30 to about 50 mm, and in the embodiment shown in FIG. 1 and FIG. 2, the length is about 45 mm.

Figure 4:
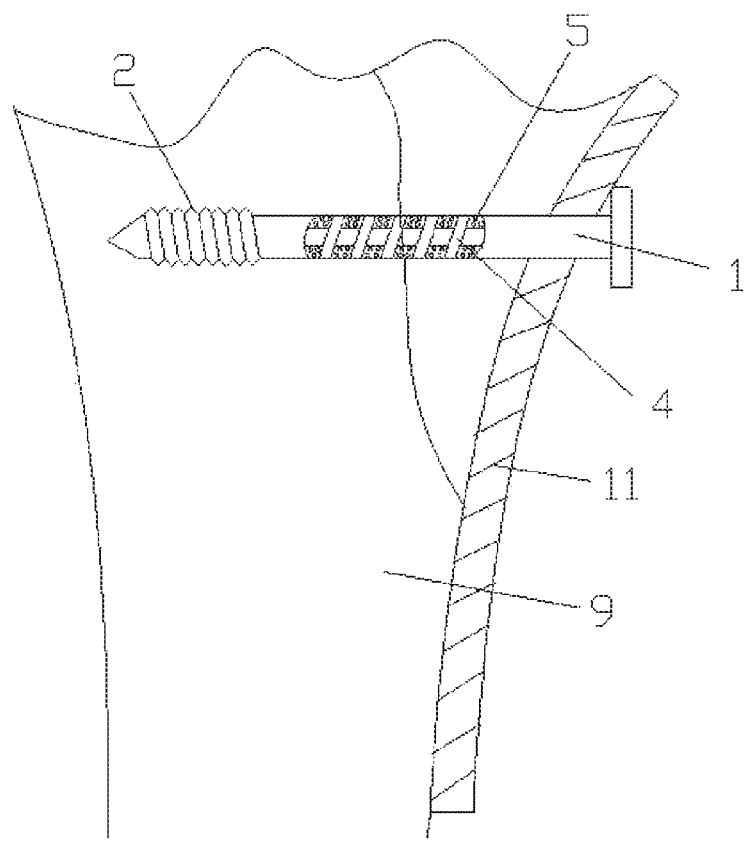
FIG. 4 is a schematic diagram showing a usage state in which the porous bionic internal fixation device for promoting healing of a fractured bone according to the present disclosure is applied to a tibial fracture.

As shown in FIG. 4, FIG. 4 is a schematic diagram showing a usage state in which the porous bionic internal fixation device for promoting healing of a fractured bone according to the present disclosure is applied to a tibial fracture. As shown in FIG. 4, the porous bionic internal fixation device for promoting healing of a fractured bone according to the present disclosure includes a tensile fixation nail 1 and a connection steel plate 11, and the steel plate 11 is provided with a hole for passing through the tensile fixation nail 1. When the fractured tibia 9 is reduced and fixed, the tensile fixation nail 1 has an internal fixation thread 2 at one end and a nail head at the other end, the end of the tensile fixation nail 1 having the internal fixation thread 2 is inserted through the hole on the connection steel plate 11 to connect the fractured outside tibia 9 with the fractured inside tibia 9, and the locking structure on the other end of the tensile fixation nail 1 is located at outside of the fractured outside tibia 9 and the connection steel plate 11, the apertures 4 of the tensile fixation nail 1 are positioned at both sides of the fractured bone of the tibia 9. The apertures 4 and micro-holes 5 on the tensile fixation nail 1 may be respectively arranged to be consistent with the direction of the tensile bone trabeculae and the compressive trabeculae.

Figure 5:
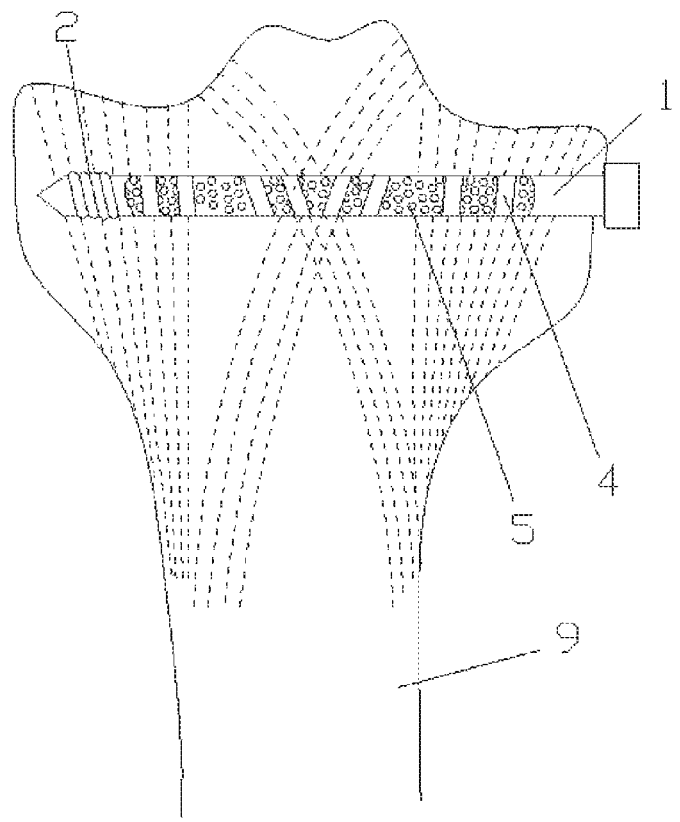
FIG. 5 is a schematic diagram showing a usage state in which the porous bionic internal fixation device for promoting healing of a fractured bone according to the present disclosure is applied to another tibial fracture.

As shown in FIG. 5, FIG. 5 is a schematic diagram showing a usage state in which the porous bionic internal fixation device for promoting healing of a fractured bone according to the present disclosure is applied to another tibial fracture. The embodiment shown in FIG. 5 is different from that in FIG. 4 only in that the connection steel plate 11 is omitted, other structures are identical with that in FIG. 4, and thus will not be further described herein.

Figure 6:
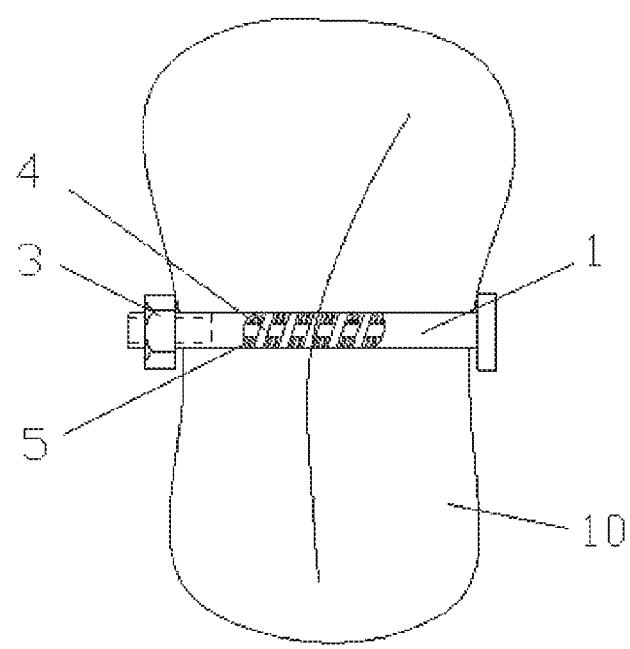
FIG. 6 is a schematic diagram showing a usage state in which the porous bionic internal fixation device for promoting healing of a fractured bone according to the present disclosure is applied to a calcaneal fracture.

As shown in FIG. 6, FIG. 6 is a schematic diagram showing a usage state in which the porous bionic internal fixation device for promoting healing of a fractured bone according to the present disclosure is applied to a calcaneal fracture. As shown in FIG. 6, when a fractured calcaneus 10 is fixed, two ends of the tensile fixation nail 1 are respectively located at opposite sides of the calcaneus 10, one end of the tensile fixation nail 1 is provided with a thread on which a locking nut 3 is provided, the other end of the tensile fixation nail 1 is provided with a nail head, the fractured calcaneus 10 may be fixed by the locking nut, and the apertures 4 of the tensile fixation nail 1 are positioned at opposite sides of the fractured bone of the calcaneus 10.

The tensile fixation nail 1 according to the present disclosure, as an internal fixation implantation, may be made from both absorbable material and non-absorbable material. The tensile fixation nail 1 made from absorbable material is suitable for aged people who has relative low bone strength, has relative light load and good histocompatibility, and avoids impairment from reoperation. The tensile fixation nail 1 made from non-absorbable material is suitable for the young and mid-aged patients, by using titanium group material having relative good histocompatibility, the tensile fixation nail 1 may have relative low ionization reaction, high internal fixation strength, light rejection, and needs not to be taken out.

INDUSTRIAL APPLICABILITY

In the present disclosure, the bionic internal fixation theory is employed, and the bionic internal fixation device more complying with the bone autonomy structure, in particularly complying with the biomechanics structure characteristics may be used, so that the fractured bone may be recovered following its own conduction and load characteristics, and the fracture treatment may achieve the satisfactory reduction and healing result. With the creative invention of the fracture reduction and fixation technology according to the present disclosure, the problem that the cancellous bone is poorly healed after the treatment of the fracture, especially, the osteoporotic fracture of an aged people, the healing strength of the bone is influenced, and sometimes, possibly to cause the delay healing of the fractured bone or even re-fracture, is solved.

The present disclosure has been described with reference to several exemplary embodiments, but, it should be understood that the terms as used herein is only illustrative and exemplary rather than limitation. Since the present disclosure may be particularly carried out in various forms without departing from the spirit or substance of the present disclosure, it should be understood that the above embodiments would never be limited to any details as above described, rather, should be interpreted broadly according to the spirit and scope as defined in the following claims, therefore, all the variations and modifications fallen within the scope of claims and its equivalents should be covered by the following claims.

What is claimed is:

1. A porous bionic internal fixation device for promoting healing of a fractured bone, wherein the porous bionic internal fixation device comprises a lag screw in round rod shape, the lag screw is provided with fixation structures at both ends thereof, a plurality of apertures directing laterally or obliquely are provided on a body of the lag screw, and between adjacent apertures of the plurality of apertures, densely distributed micro-holes are provided on the body of the lag screw, wherein each of the plurality of apertures has a slimline shape, each of the densely distributed micro-holes is a through hole that extends through an outer surface of the lag screw into an interior of the lag screw, when in use, the both ends of the lag screw are respectively located in bones at opposite sides of the fractured bone, so that a longitudinal direction of each of the plurality of apertures is consistent with a direction of tensile trabeculae and/or compressive trabeculae at the fractured bone and the position of each of the plurality of apertures corresponds to the fractured bone.

2. The porous bionic internal fixation device for promoting healing of a fractured bone according to claim 1, wherein the plurality of apertures are arranged in parallel along longitudinal direction, or transverse direction, or oblique direction of the lag screw.

3. The porous bionic internal fixation device for promoting healing of a fractured bone according to claim 2, wherein further comprising:
a femur fixation main nail, wherein the femur fixation main nail is provided with a connection through hole in which the lag screw is inserted, an angle between the femur fixation main nail forms and the lag screw is 90 degree to 140 degree, and the femur fixation main nail is provided with a through hole along its transverse direction.

4. The porous bionic internal fixation device for promoting healing of a fractured bone according to claim 2, wherein further comprising a connection steel plate on which a hole for passing the lag screw is provided.

5. The porous bionic internal fixation device for promoting healing of a fractured bone according to claim 2, wherein the fixation structure at one end of the lag screw is a fixation thread or a locking nut for engaging with a thread on the lag screw, and the fixation structure at the other end is a fixation thread or a nail head integrated with the lag screw.

6. The porous bionic internal fixation device for promoting healing of a fractured bone according to claim 1, wherein each of the plurality of apertures each has a diameter of 0.1 to 3 mm, and each of the densely distributed micro-holes each has a diameter of 1 to 50 um.

7. The porous bionic internal fixation device for promoting healing of a fractured bone according to claim 1, wherein when in use, each of the plurality of apertures positioned at the fractured bone are respectively consistent with the directions of primary tensile trabeculae, secondary tensile trabeculae, primary compressive trabeculae and secondary compressive trabeculae at the local bone.

8. The porous bionic internal fixation device for promoting healing of a fractured bone according to claim 1, wherein each of the plurality of apertures and/or each of the plurality of densely distributed micro-holes are filled with magnesium alloy for promoting healing of the fractured bone.

9. The porous bionic internal fixation device for promoting healing of a fractured bone according to claim 8, wherein further comprising:
a femur fixation main nail, wherein the femur fixation main nail is provided with a connection through hole in which the lag screw is inserted, an angle between the femur fixation main nail forms and the lag screw is 90 degree to 140 degree, and the femur fixation main nail is provided with a through hole along its transverse direction.

10. The porous bionic internal fixation device for promoting healing of a fractured bone according to claim 8, wherein further comprising a connection steel plate on which a hole for passing the lag screw is provided.

11. The porous bionic internal fixation device for promoting healing of a fractured bone according to claim 8, wherein the fixation structure at one end of the lag screw is a fixation thread or a locking nut for engaging with a thread on the lag screw, and the fixation structure at the other end is a fixation thread or a nail head integrated with the lag screw.

12. The porous bionic internal fixation device for promoting healing of a fractured bone according to claim 1, wherein the lag screw is provided with a through hole along its longitudinal direction.

13. The porous bionic internal fixation device for promoting healing of a fractured bone according to claim 1, wherein further comprising:
a femur fixation main nail, wherein the femur fixation main nail is provided with a connection through hole in which the lag screw is inserted, an angle between the femur fixation main nail forms and the lag screw is 90 degree to 140 degree, and the femur fixation main nail is provided with a through hole along its transverse direction.

14. The porous bionic internal fixation device for promoting healing of a fractured bone according to claim 13, wherein a plurality of apertures are provided on the femur fixation main nail, a longitudinal direction of each of the plurality of apertures is consistent with the direction of the primary tensile trabeculae or compressive trabeculae at the fractured bone, the position of the apertures corresponds to the fractured bone, and between adjacent apertures of the plurality of apertures, densely distributed micro-holes are provided on a body of the femur fixation main nail.

15. The porous bionic internal fixation device for promoting healing of a fractured bone according to claim 13, wherein the femur fixation main nail is provided with a notch at one end thereof, and the notch is perpendicular to a central line of the femur fixation main nail.

16. The porous bionic internal fixation device for promoting healing of a fractured bone according to claim 13, wherein each of the plurality of apertures and/or each of the plurality of densely distributed micro-holes provided on the femur fixation main nail are filled with magnesium alloy for promoting healing of the fractured bone.

17. The porous bionic internal fixation device for promoting healing of a fractured bone according to claim 13, wherein each of the plurality of apertures on the femur fixation main nail is arranged along the longitudinal direction of the femur fixation main nail in parallel.

18. The porous bionic internal fixation device for promoting healing of a fractured bone according to claim 13, wherein each of the plurality of apertures on the femur fixation main nail has a diameter of 0.1 to 0.3 mm, and each of the plurality of densely distributed micro-holes on the femur fixation main nail
has a diameter of 1 to 50 um.

19. The porous bionic internal fixation device for promoting healing of a fractured bone according to claim 1, wherein further comprising a connection steel plate on which a hole for passing the lag screw is provided.

20. The porous bionic internal fixation device for promoting healing of a fractured bone according to claim 1, wherein the fixation structure at one end of the lag screw is a fixation thread or a locking nut for engaging with a thread on the lag screw, and the fixation structure at the other end is a fixation thread or a nail head integrated with the lag screw.

* * * * *